United States Patent [19]

Wurtman et al.

[11] 4,210,637
[45] Jul. 1, 1980

[54] COMPOSITION AND METHOD FOR SUPPRESSING APPETITE FOR CALORIES AS CARBOHYDRATES

[75] Inventors: Richard J. Wurtman; Judith J. Wurtman, both of Waban; John D. Fernstrom, Boston, all of Mass.

[73] Assignee: Massachusetts Institute of Technology, Cambridge, Mass.

[21] Appl. No.: 929,387

[22] Filed: Jul. 31, 1978

[51] Int. Cl.$^2$ ............................................. A61K 31/70
[52] U.S. Cl. ........................................ 424/180; 536/1
[58] Field of Search ....................... 536/1, 4; 424/180

[56] References Cited

U.S. PATENT DOCUMENTS

| | | | |
|---|---|---|---|
| 3,773,930 | 11/1973 | Mohammed et al. | 424/180 |
| 3,843,786 | 10/1974 | Wong | 424/180 |
| 3,856,942 | 12/1974 | Murphy | 424/180 |
| 3,989,822 | 11/1976 | Whistler | 424/180 |
| 4,009,265 | 2/1977 | Howard | 424/180 |
| 4,085,207 | 4/1978 | Aoki et al. | 424/180 |

*Primary Examiner*—Johnnie R. Brown
*Assistant Examiner*—Blondel Hazel
*Attorney, Agent, or Firm*—Arthur A. Smith, Jr.; Paul J. Cook

[57] ABSTRACT

A composition, comprising tryptophan and an insulin-releasing carbohydrate, is administered to an animal prior to consuming food; this suppresses total caloric intake while having only a small effect on protein intake.

17 Claims, No Drawings

COMPOSITION AND METHOD FOR SUPPRESSING APPETITE FOR CALORIES AS CARBOHYDRATES

BACKGROUND OF THE INVENTION

The government has rights in this invention pursuant to Grant No. Am 14228 awarded by the National Institute of Health.

This invention relates to a method and composition for suppressing calorie consumption by animals.

Presently, appetite is suppressed in order to control intake of calories by administering certain drugs or bulking substances. Commonly, drugs like dexedrine or d-amphetamine have been administered orally and have been found effective in suppressing appetite. However, each of these drugs has unwanted side effects (such as induction of hyperactivity or even psychosis) and in some instances can be dangerous to the user. In addition, the amphetamines do not exhibit selectivity in suppressing calorie-carbohydrate intake as they also cause a suppression in protein consumption. This feature makes them disadvantageous, especially in obese adolescents. Similarly, the use of carbohydrates or bulking substances have been found to be relatively ineffective in suppressing appetite.

It would be highly desirable to provide a means for suppressing appetite in a selective manner such that the appetite for high caloric foods is suppressed while at the same time appetite for protein substances is less affected. Furthermore, it would be desirable to provide such a means which does not exhibit unwanted side effects such as those that occur with drugs such as the amphetamines.

SUMMARY OF THE INVENTION

The present invention provides a method and composition for suppressing appetite for calories (as carbohydrates) while elevating the percent of total calories that is consumed as protein. This invention is based upon the discovery that a combination of tryptophan and a carbohydrate (which causes insulin secretion) selectively suppresses the appetite for calories (as carbohydrates). The mixture of tryptophan and an insulin-secreting carbohydrate can be administered alone, in admixture with one or more amino acids normally found in the blood plasma, or with caffeine or another mild stimulant, to override the mixture's natural sedating effects. It is believed that these compositions function by mechanisms which involve the enhancement of brain serotonin synthesis; this neurotransmitter is involved in the control of appetite. A particular useful second amino acid is tyrosine, which is a precursor for dopamine and norepinephrine in synapses. Thus, a composition of this invention which also includes tyrosine permits serotonin synthesis to be accelerated while not reducing the synthesis of dopamine and/or norepinephrine in synapses; in some situations, such as when it is necessary to be fully attentive, it is important not to lower dopamine and/or norepinephrine synthesis.

DETAILED DESCRIPTION OF THE SPECIFIC EMBODIMENTS

In accordance with this invention, tryptophan and an insulin-releasing carbohydrate are administered to a patient either alone or in combination with one or more other amino acids normally found in the blood plasma. When there is need to sustain or increase brain dopamine or norepinephrine levels, these compositions also contain tyrosine in addition to the tryptophan and the carbohydrate that causes insulin to be released. The administration of tryptophan changes the ratio of tryptophan to the sum of the plasma concentrations of other neutral amino acids that compete with tryptophan for uptake in the brain thereby increasing the brain serotonin level. Furthermore, the administration of a carbohydrate that releases insulin decreases the plasma levels of the other neutral amino acids normally found in the plasma such a leucine, isoleucine, tyrosine, phenylalanine and valine. Thus, the carbohydrate causes an increase of the plasma levels of tryptophan in relation to these other amino acids by decreasing the concentration of the other amino acids in the plasma. Both of these effects are cumulative in effecting an increase in brain serotonin levels. While applicants do not intend to be bound by a theory of the mechanism of this invention, it is believed that increases in brain serotonin levels operate to cause a selective suppression of appetite for calories.

Representative suitable carbohydrates for this invention include sucrose, dextrose, starch, fructose, invert sugar, dextrins, sugar polymers such as polyose, xylitol and mixtures thereof or the like. The relative proportion of tryptophan to the insulin-releasing carbohydrate can vary widely so long as that there is a cumulative affect on brain serotonin levels by the two components utilized in the composition of this invention. Generally, the weight ratio of the tryptophan to the carbohydrate(s) is between about 0.05 and about 5.0, more usually between about 0.20 and about 2.0. The compositions of this invention are administered in an amount sufficient to effect increase in brain serotonin levels while not being administered in such large amounts as to serously reduce the brain levels of other neurotransmitters needed for normal functioning such as dopamine, norepinephrine, acetylcholine, or the non-essential amino acids. Generally, the compositions of this invention are administered in an amount of between about 10 mg/kg and about 100 mg/kg of tryptophan, and 10 mg/kg and 300 mg/kg of carbohydrate, more usually between 20 mg/kg and about 50 mg/kg of tryptophan, and 30 mg/kg and 150 mg/kg of carbohydrate. Typical unit dosage form useful for oral administration ranges between about 0.5 grams and about 15 grams, and more usually between about 1 grams and about 10 grams.

The tryptophan and other neutral amino acids can be administered as free amino acids, esters, salts neutral or synthetic polymers or as constituents of food. The route of administration will generally be oral, for example, as a tablet, sustained-release capsule, drink, beverage sweetner, wafer, candy, chewing gum. It may be mixed with a mild stimulant like caffeine for daytime use (to override the sedative effect of tryptophan), or used without a mild stimulant at nighttime (for example, by people with nocturnal eating problems).

The following example illustrates the present invention and is not intended to limit the same.

EXAMPLE I

This example illustrates that the administration of a diet containing an insulin-releasing carbohydrate and tryptophan effects a reduction in appetite for carbohydrates.

Male Sprague-Dally rats (Charles River Breeding Laboratory, wilmington, Mass.) weighing 130 grams were housed in cages (1 per cage), and given ad libitum access to tap water and, for 8 hours each day, two test diets comprising protein (casein), corn oil, carbohydrate (dextrin), vitamins and minerals. One of the test diets contained 5% protein and the other test diet contained 45% protein. The rats were maintained under light (300 microwatts/cm$^2$); Vita-Lite, Duro-Test Corp., Northburg, N.J., between 8:00 a.m. and 8:00 p.m. daily. The control values obtained in Table I below are from data obtained on the same rats as used during the actual test on the day preceding administration of the tryptophan and sucrose.

After the control data were obtained, each of the rats was given a 3 gram mixture containing 1.5 grams sucrose, 30 mg tryptophan and 1.5 ml water. This diet was consumed within 15 minutes and 30 minutes thereafter each of the rats was given access to the two test diets containing respectively 5% and 45% protein. Food consumption by each rat was measured 45 minutes after the animals had been given access to the test diets. The results are shown in Table I. As shown in Table I, each of the rats given the three meal diet containing tryptophan and sucrose consumed approximately 50% less carbohydrate food on the average as compared to the control data.

TABLE I

| Group | Food Intake (grams) | %-Protein Ingested |
|---|---|---|
| Control | 10.5 ± 1.0 | 25.0 ± 1.7 |
| Pre-meal | 5.6 ± 1.0* | 31.0 ± 1.8** |

*P < 0.001
**P < 0.02

We claim:

1. A composition which, when administered to an animal, decreases appetite for calories as carbohydrates which consists essentially of an amount of tryptophan effective to increase brain serotonin levels and a carbohydrate in an amount effective to cause insulin to be released in the animal.

2. The composition of claim 1 wherein the carbohydrate is a sugar.

3. The composition of claim 2 wherein the sugar is sucrose.

4. A composition which, when administered to an animal decreases appetite for calories as carbohydrates consisting essentially of an amount of tryptophan effective to increase brain serotonin levels, a carbohydrate in an amount effective to cause insulin to be released in the animal and tyrosine in an amount effective to maintain or increase brain dopamine and/or norepinephrine levels in the animal.

5. The composition of claim 4 wherein the carbohydrate is a sugar.

6. The composition of claim 5 wherein the sugar is sucrose.

7. The composition of claim 1 which includes caffeine.

8. The method of using a composition consisting essentially of tryptophan and a carbohydrate for decreasing appetite in an animal for calories as carbohydrates which comprises administering to the animal a composition consisting essentially of an amount of tryptophan effective to increase brain serotonin levels and a carbohydrate in an amount effective to cause insulin to be released in the animal.

9. The method of claim 8 wherein the carbohydrate is a sugar.

10. The method of claim 9 wherein the sugar is sucrose.

11. The method of claim 8 wherein the composition includes tyrosine in an amount effective to maintain or increase brain dopamine and/or norepinephrine levels.

12. The method of claim 11 wherein the carbohydrate is a sugar.

13. The method of claim 12 wherein the sugar is sucrose.

14. The process of claim 8 wherein the composition includes caffeine.

15. The process of claim 13 wherein the composition includes caffeine.

16. A composition which, when administered to an animal, decreases appetite for calories as carbohydrates consisting essentially of an amount of tryptophan effective to increase brain serotonin levels in the animal, a carbohydrate in an amount effective to cause insulin to be released in the animal, and caffeine.

17. A composition which, when administered to an animal, decreases appetite for calories as carbohydrates which comprises an amount of tryptophan effective to increase brain serotonin levels in the animal, a carbohydrate in an amount effective to cause insulin to be released in the animal, tyrosine in an amount effective to maintain or increase brain dopamine and/or norepinephrine levels in the animal and caffeine.

* * * * *